US011612564B2

(12) United States Patent
Haley

(10) Patent No.: US 11,612,564 B2
(45) Date of Patent: Mar. 28, 2023

(54) BILAYER ADHERING LOZENGE EFFECTIVE TO MASK UNDESIRABLE FLAVOR

(71) Applicants: Quest Products, LLC, Pleasant Prairie, WI (US); Jeffrey Haley, Seattle, WA (US)

(72) Inventor: Jeffrey Haley, Seattle, WA (US)

(73) Assignee: Quest Products, LLC, Pleasant Prairie, WI (US)

(*) Notice: Subject to any disclaimer, the term of this patent is extended or adjusted under 35 U.S.C. 154(b) by 77 days.

(21) Appl. No.: 16/467,144

(22) PCT Filed: Apr. 19, 2019

(86) PCT No.: PCT/US2019/028290
§ 371 (c)(1),
(2) Date: Jun. 6, 2019

(87) PCT Pub. No.: WO2019/204708
PCT Pub. Date: Oct. 24, 2019

(65) Prior Publication Data
US 2021/0022998 A1 Jan. 28, 2021

Related U.S. Application Data

(60) Provisional application No. 62/660,964, filed on Apr. 21, 2018.

(51) Int. Cl.
*A61K 9/00* (2006.01)
*A61K 9/24* (2006.01)
*A61K 47/36* (2006.01)

(52) U.S. Cl.
CPC ............ *A61K 9/0056* (2013.01); *A61K 9/006* (2013.01); *A61K 9/209* (2013.01); *A61K 47/36* (2013.01)

(58) Field of Classification Search
CPC ...... A61K 9/20; A61K 9/2004; A61K 9/2081; A61K 9/2086; A61K 9/2095; A61K 9/0002; A61K 9/0012; A61K 9/0053; A61K 9/0056; A61K 9/006
See application file for complete search history.

(56) References Cited

U.S. PATENT DOCUMENTS

| | | |
|---|---|---|
| 8,865,133 B2 | 10/2014 | Haley |
| 8,945,606 B2 | 2/2015 | Haley |
| 8,980,334 B2 | 3/2015 | Domb |
| 9,688,779 B2 | 6/2017 | Haley |
| 9,789,061 B2 | 10/2017 | Haley |
| 10,479,842 B2 | 11/2019 | Haley |
| 2003/0124178 A1 | 7/2003 | Haley |
| 2004/0156930 A1 | 8/2004 | Haley |
| 2005/0226915 A1 | 10/2005 | Haley |
| 2006/0134201 A1 | 6/2006 | Haley |
| 2007/0042027 A1 | 2/2007 | Haley |
| 2007/0059254 A1* | 3/2007 | Singh ................ A61K 31/4045 424/48 |
| 2007/0098648 A1 | 5/2007 | Haley |
| 2007/0243238 A1 | 10/2007 | Haley |
| 2007/0248654 A1 | 10/2007 | Haley |
| 2007/0248655 A1 | 10/2007 | Haley |
| 2007/0274927 A1 | 11/2007 | Haley |
| 2007/0293587 A1 | 12/2007 | Haley |
| 2009/0004248 A1* | 1/2009 | Bunick ................ A61K 9/209 424/440 |
| 2009/0010997 A1 | 1/2009 | Haley |
| 2009/0104128 A1 | 4/2009 | Haley |
| 2009/0169489 A1 | 7/2009 | Haley |
| 2010/0092543 A1 | 4/2010 | Haley |
| 2010/0285098 A1 | 11/2010 | Haley |
| 2010/0285127 A1 | 11/2010 | Barkan |
| 2011/0250281 A1 | 10/2011 | Mapelli |
| 2012/0251622 A1 | 10/2012 | Haley |
| 2015/0072005 A1* | 3/2015 | Habboushe .......... A61K 31/522 424/471 |
| 2015/0110851 A1 | 4/2015 | Haley |
| 2015/0147555 A1 | 5/2015 | Haley |
| 2015/0320787 A1 | 11/2015 | Haley |
| 2016/0184236 A1 | 6/2016 | Haley |
| 2017/0100328 A1* | 4/2017 | Kovarik ................ A61F 5/566 |
| 2017/0296487 A1 | 10/2017 | Haley |
| 2017/0319703 A1 | 11/2017 | Haley |
| 2018/0296466 A1 | 10/2018 | Haley |

FOREIGN PATENT DOCUMENTS

| | | | |
|---|---|---|---|
| WO | 0170194 | 9/2001 | |
| WO | WO-2005009386 A2 * | 2/2005 | ......... A61K 31/4439 |

OTHER PUBLICATIONS

International Search Report and Writtten Opinion issued in corresponding International Application No. PCT/US2019/028290, dated Aug. 22, 2019, 7 pages.

* cited by examiner

*Primary Examiner* — Micah Paul Young
(74) *Attorney, Agent, or Firm* — Fitch Even Tabin & Flannery LLP

(57) ABSTRACT

An oral adhering lozenge is provided which delivers to the mouth a component with an undesirable flavor and a component for delivering a masking flavor. The oral adhering lozenge comprises a first, adherent layer and a second layer. The first, adherent layer includes a flavor-masking component, and the second layer includes both an active component and a flavor-masking component. In another configuration, the first, adherent layer includes both an active component and a flavor-masking component. In use, the second layer of the lozenge generally finishes dissolving and/or eroding in the mouth before the first layer finishes dissolving and/or eroding. The later eroding adherent layer will continue to release the flavor-masking component after all of the active component has been released into the mouth, thereby providing increased masking of any bitter aftertaste of the active.

19 Claims, 1 Drawing Sheet

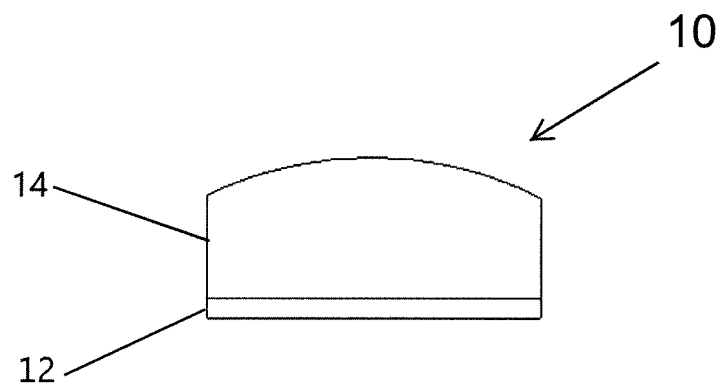

BILAYER ADHERING LOZENGE EFFECTIVE TO MASK UNDESIRABLE FLAVOR

CROSS-REFERENCE TO RELATED APPLICATION

This application claims the benefit of U.S. Provisional Application No. 62/660,964, filed Apr. 21, 2018, which is incorporated herein by reference in its entirety.

FIELD

This application relates to orally-administered adhering lozenge formulations, particularly bilayer adhering lozenges, that are effective to mask undesirable flavors of active components.

BACKGROUND

Active ingredients can be orally administered in a variety of forms, including in the form of a syrup, lozenge, capsule, tablet, and spray. Many active ingredients provide bitter, astringent, medicinal, metallic, or other off-flavor notes, so oral formulations often include a flavoring agent, such as a sweet, mint, or cinnamon flavor, to help mask the bad flavor and increase consumer acceptance of the product. Unfortunately, even with a flavoring agent, bitter and other off-flavors often linger in the mouth and create an unappealing aftertaste that reduces consumer acceptance or enjoyment of the product. In particular, children may reject a bitter-tasting medicament, nutraceutical, or other orally ingestible product.

Oral adhering lozenges can be used to adhere in the mouth and slowly release active ingredients as they dissolve. They are typically adhered to the outside of a molar or gums alongside the outside of a molar. Sometimes the active ingredient has an undesirable flavor that needs to be masked. As the adhering lozenge dissolves, it releases both the undesirable flavor and the masking flavor. If the undesirable flavor lingers in the mouth longer than the masking flavor, then the undesirable flavor predominates the after taste.

There remains a need for formulations of oral adhering lozenges that better mask undesirable flavors from active components.

SUMMARY

Provided herein are oral adhering lozenges and methods of making lozenges effective to mask an undesirable flavor from one or more active components in the lozenge.

In one aspect, an oral adhering lozenge is provided which delivers to the mouth a component with an undesirable flavor and a component for delivering a masking flavor. The oral adhering lozenge comprises at least a first, adherent layer and a second layer. The first, adherent layer includes a flavor-masking component, and the second layer includes both an active component and a flavor-masking component. In another configuration, the first, adherent layer includes both an active component and a flavor-masking component.

In use, the second layer of the lozenge generally finishes dissolving and/or eroding in the mouth before the first layer finishes dissolving and/or eroding. The later eroding adherent layer will continue to release the flavor-masking component after all of the active component has been released into the mouth, thereby providing increased masking of any bitter aftertaste of the active.

In one aspect, an oral adhering lozenge is provided with a flavor masking component that is effective to mask an undesirable flavor from an active component in the lozenge. The lozenge comprises a first, adherent layer having a first and second side and comprising an adhesive component and a flavor-masking component that is released as the first layer dissolves and/or erodes in a human mouth. Adhered to a second side of the first layer is a second layer comprising an active component with an undesirable flavor and a flavor-masking component that are released as the second layer dissolves and/or erodes in the human mouth. The first layer is configured to be adhered to the inside of the mouth, and, when adhered in the human mouth, the second layer finishes dissolving and/or eroding before the first layer finishes dissolving and/or eroding. If the adherent layer also comprises an active component, a ratio of the amount of flavor-masking component to active component in the adherent layer is higher than a ratio of the amount of flavor-masking component to active component in the second layer.

In one approach, the first, adherent layer further comprises an active component with an undesirable flavor. In another approach, the first, adherent layer includes no active component.

In another aspect, the perceivable amount of flavor-masking component is higher in the first, adherent layer than in the second layer.

The flavor-masking component may be homogeneously distributed in one or more of the layers of the lozenge, and the active component may be homogeneously distributed in one or more of the layers of the lozenge. In one aspect, the flavor-masking component is homogeneously dispersed in the first, adherent layer. In another aspect, the flavor-masking component is homogeneously dispersed in the second layer. In another aspect, the active component is homogeneously dispersed in the second layer. In another aspect, the active component is homogeneously dispersed in the first, adherent layer. In another aspect, the flavor-masking component and active component are both homogeneously dispersed in the first, adherent layer. In another aspect, the flavor-masking component and active component and active component are both homogeneously dispersed in the second layer.

Also provided herein is a method for preparing a bilayer oral adhering lozenge effective to mask an undesirable flavor from an active component. The method includes mixing powders and/or granules comprising an adhesive component and a flavor-masking component for a first, adherent layer. Powders and/or granules comprising an active component having an undesirable flavor and a flavor-masking component for a second layer are also mixed. The mixtures for the first, adherent layer and second layer in a bi-layer tablet are pressed to form a bilayer adhering lozenge. If an active component is included in the mixture for the first, adherent layer, a ratio of the amount of flavor-masking component to active component in the adherent layer is higher than a ratio of the amount of flavor-masking component to active component in the second layer. In some approaches, the amount of active component in the first, adherent layer is zero. In a preferred aspect, the adhesive component comprises acacia gum. In yet another approach, the ratio of amounts of flavor-masking components to active components are the perceivable amounts of the flavor of each component.

In one aspect, the method further includes granulating the active component having an undesirable flavor and the flavor-masking component together to form granules having a homogeneous mixture of the active component and flavor-masking component for forming the second layer. The method may also include granulating the flavor-masking component with one or more excipients to form granules having a homogeneous mixture of the flavor-masking component for forming the first, adherent layer. In another aspect, the method may further include coating the active component having an undesirable flavor onto grains of a binder to form granules.

In the methods and lozenges described herein, the flavor-masking component may comprise one or more of a flavor oil, sweetener, flavor compound, polyol, flavor essence, fruit extract, or combination thereof, and the active component may comprise one or more of an antibiotic, aspirin, anti-inflammatory, antacid, vitamin, cannabidiol, antifungal, nicotine, caffeine, chamomile, and combinations thereof.

BRIEF DESCRIPTION OF THE DRAWING

The FIGURE shows a side view of a bi-layer adhering lozenge.

Elements in the FIGURE are illustrated for simplicity and clarity and have not necessarily been drawn to scale. For example, the dimensions and/or relative positioning of some of the elements in the FIGURE may be exaggerated relative to other elements to help to improve understanding of various embodiments.

DETAILED DESCRIPTION

Adhering lozenges are effective for releasing active ingredients in the mouth for various purposes, such as to topically treat the mouth lining, to achieve absorption into the mouth lining, or for penetration through the mouth lining into the blood. Disclosed herein are oral adhering lozenge compositions which release an active component with an undesirable flavor (e.g., bitter flavor) and at least one flavor-masking component. The oral adhering lozenge, when held in the mouth, is configured to erode and release the component with an undesirable flavor along with a flavor-masking component. The oral adhering lozenges may be adhered onto the mouth mucosa, teeth, or gums, and the components of the lozenge are released into saliva in the mouth or into the mucosa. Particles of the active component within the lozenge are progressively exposed at the eroding surface of the lozenge. Erosive forces at the surface of the lozenge, such as from rubbing against mucosa, teeth, and the tongue will release particles of the active component. Additionally, saliva flow in the mouth causes the lozenge to dissolve. Advantageously, the lozenges described herein are effective to mask an undesirable flavor of an active component in the lozenge as it is released in the oral cavity.

The oral adhering lozenges described herein may also be referred to as an oral adhering disc or troche. The FIGURE shows an exemplary bilayer adhering lozenge 10. The adhering lozenge 10 includes a first, adherent layer 12 and a second layer 14. The first, adherent layer 12 has at least a first side and a second side. When applied to a user's mouth, the first side of the adherent layer would be placed against an interior surface of the mouth (e.g., the mucosa, tooth, and/or gums). The second side of the adherent layer is adhered to the second layer 14 of the bilayer adhering lozenge.

In one configuration, the first, adherent layer includes a flavor-masking component, and the second layer includes both an active component and a flavor-masking component. In use, the second layer of the lozenge generally finishes dissolving and/or eroding in the mouth before the first, adherent layer finishes dissolving and/or eroding. In this approach, the later eroding adherent layer will continue to release the flavor-masking component after all of the active component has been released into the mouth, thereby providing increased masking of any bitter or otherwise undesirable aftertaste of the active.

In another configuration, the first, adherent layer includes both an active component and a flavor-masking component, and the second layer includes both an active component and a flavor-masking component. In use, both the active component and flavor-masking component are released as the second layer erodes and then again as the first, adherent layer erodes. In this approach, it is particularly preferred that the ratio of flavor-masking component to active component is higher in the first, adherent layer than in the second layer, thereby providing increased release of the flavor-masking component as the lozenge degrades in the mouth and also providing increased masking of any bitter aftertaste of the active component.

In one aspect, the relative amounts of flavor-masking component in the adherent layer and the second layer may be the perceivable amount of flavor-masking component rather than a total weight of a flavor-masking component in that layer. For example, a small amount of a strongly flavored flavor-masking component in the adherent layer may provide more perceivable flavor than a larger amount of a more weakly flavored flavor-masking component in the second layer of the lozenge. Further, the ratio of flavor-masking component to active component that is higher in the first, adherent layer than the ratio of flavor-masking component to active component in the second layer may be the perceivable amount of flavor provided by the flavor-masking component versus the bitter or other off-flavor provided by the active component. In either respect, the perceivable amount of flavor provided by either the flavor-masking component or the active component may be determined by a team of trained sensory panelists using a triangle test in accordance with procedures set forth by the Society of Sensory Professionals. An appropriate test includes the following. A panelist is provided with one different and two alike samples at the same time. The panelist is instructed to taste the samples from left to right. All six order combinations (AAB, ABA, BAA, BBA, BAB, and ABB) should be randomized across panelists. In this test, "A" could be the first, adherent layer and "B" could be the second layer. The panelist is instructed to identify the odd sample and record the answer. The results can be analyzed with the chi-square distribution using the formula $X^2=\Sigma(|O-E|)^2/E$, where O=observed and E=expected.

As described herein, the flavor-masking component may be the same or different in the respective layers of the lozenge. In another aspect, the active component may be the same or different in the respective layers of the lozenge.

Active Component

In one aspect, the active component with an undesirable flavor may be an active agent, such as an active pharmaceutical ingredient ("API"), that can be delivered orally by absorption through mucous membranes of the oral cavity. The active agent may be a therapeutic agent, such as in the form of an inorganic compound, organic compound, peptide, protein, carbohydrate, amino acids, fatty acids, minerals, and any combination thereof. Exemplary active agents with undesirable flavors include, for example, antibiotic, aspirin, anti-inflammatory, antacid, vitamin, cannabidiol (CBD), antifungal (e.g., Nystatin, Clotrimazole), nicotine, caffeine, and chamomile.

For example, the active component may comprise cannabidiol (CBD), which can be extracted from hemp plants but CBD has a bitter taste that can be undesirable in an orally administered composition. Adhering lozenges according to the present disclosure may incorporate any form of cannabidiol, such as powders, grains, crystals, nanoparticles, or a combination thereof.

Flavor-Masking Component

The flavor-masking component may be any ingredient that is effective, either alone or in combination with another component, to mask an unappealing flavor provided by the active ingredient. The flavor-masking ingredient may simply cover an undesirable flavor of the active component or it may also provide a characteristic flavor (e.g., a mint flavor) to the lozenge. For example, the flavor-masking component may include one or any combination of sweeteners, flavor compounds, polyol, flavor oils, flavor essences, or fruit extracts described herein. The flavor-masking component may be synthetically produced or naturally derived, such as from a fruit or spice.

In one approach, the masking flavor may be a sweet flavor, such as from sugar, polyol, nutritive sweetener, or non-nutritive sweetener. As used herein, the term "nutritive sweetener" includes fructose syrup, agave syrup, sugars (e.g., monosaccharides, disaccharides), glucose syrup, sucrose syrup, lactose syrup, carbohydrate syrup, and combinations thereof. In some approaches, it may not be desired to include nutritive sweeteners because such sweeteners may contribute to the development of dental caries over time.

As used herein, the term "non-nutritive sweetener" includes sweeteners commonly referred to as "high intensity sweeteners." For example, the non-nutritive sweetener may include as aspartame, sucralose, saccharin, acesulfame potassium (Ace-K), neotame, advantame, cyclamate, alitame, neohesperidin dihydrochalcone, N—[N-[3-(3-hydroxy-4-methoxyphenyl)propyl]-L-a-aspartyl]-L-10 phenylalanine 1-methyl ester, N—[N-[3-(3-hydroxy-4-methoxyphenyl)-3-methylbutyl]-L-a-aspartyl]-L-phenylalanine 1-methyl ester, N—[N-[3-(3-methoxy-4-hydroxyphenyl)propyl]L-a-aspartyl]-L-phenylalanine 1-methyl ester, and salts thereof, and steviol glycoside sweeteners, such as rebaudioside A, rebaudioside B, rebaudioside C, rebaudioside D, rebaudioside E, rebaudioside F, dulcoside A, dulcoside B, rubusoside, stevioside, and steviolbioside. Some non-nutritive sweeteners have been found to contribute their own off-flavors to products, particularly when used in increasing amounts. Therefore, at least in some approaches, the particular non-nutritive sweetener and the amount of the sweetener should be selected so as to not provide undesirable bitter flavor to the lozenge.

In another approach, the flavor-masking component may comprise a flavor oil, such as sweet mint oil, spearmint oil, almond oil, lavender oil, rose oil, peppermint oil, wintergreen oil, cinnamon oil, eucalyptus oil, ginger oil, lemongrass oil, or a combination thereof. The flavor-masking component may also comprise an oleoresin, if desired.

In yet another approach, the flavor-masking component may comprise a fruit flavor, fruit essence, or fruit extract, such as apricot, blackberry, lemon, orange, grape, tangerine, lime, grapefruit, grape, apple, pear, strawberry, pineapple, peach, mango, melon, blood orange, lychee, papaya, cherry, guava, blueberry, plum, kiwi, pomegranate, and combinations thereof. Other non-fruit flavors could also be used, if desired. For example, the flavor-masking component may comprise a coffee, cocoa, coconut, vanilla, hazelnut, caramel, or macadamia flavor, and combinations thereof.

In yet another approach, the flavor-masking component may comprise a specific flavor compound, such as α-irisone, allyl caproate, anethole, iso-amyl acetate, iso-amyl butyrate, benzyl alcohol, butyl cinnamate, carvone, cinnamic alcohol, citral, gamma-decalactone, β-damascenone, decanal, decanol, γ-undecalactone, diacetyl, dihydroanethole, ethyl acetate, ethyl butyrate, ethyl cinnamate, ethyl salicylate, eucalyptol, ethyl maltol, eugenol, geranial, geraniol, heliotropine, 4-cis-heptenal, ionone, limonene, linalool, maltol, 1-menthyl acetate, menthone, methyl anthranilate, methyl-p-tert-butyl phenyl acetate, methyl cinnamate, methyl salicylate, neral, nerol, gamma-nonalactone, oxanone, octanol, octanal, phenylethyl alcohol, propenyl guaethol, α-terpineol, thymol, or a combination thereof.

In yet another approach, the flavor-masking component may include one or more polyols (i.e., sugar alcohols). In one aspect, the polyol may include any polyol that is solid at room temperatures such as xylitol, erythritol, sorbitol, mannitol, maltitol, isomalt, and lactitol. In some embodiments, the polyol may be provided in the form of a powder comprising polyol crystals. Advantageously, polyols are not readily converted to acids by bacteria in the mouth and, thus, do not contribute to tooth decay.

The flavor-masking component may be provided in a variety of forms, such as in a powder (e.g., extruded, spray-dried, agglomerated, freeze-dried, and encapsulated flavorings), liquid (including, for example, flavorings containing ethanol or propylene glycol), or flavor emulsions (e.g., nano- and micro-emulsions). If not in powder form, the flavor component may be combined with a carrier (such as acacia gum, dextrin, maltodextrin, or cellulose gum to form a powder.

It is noted that certain flavor components, such as a polyol, may not be sufficient by itself to mask a particular active component having an undesirable flavor. In this respect, the polyol may be considered a secondary flavor-masking component and the lozenge may further comprise a primary flavor-masking component. As used herein, a primary flavor-masking component has a much stronger perceptible flavor by weight of the component than a secondary flavor-masking component. For example, 1 gram of flavor oil may have a stronger orally-perceptible flavor than 1 gram of xylitol.

Adhesive Component

The first, adherent layer comprises an adhesive component to adhere the lozenge to a surface in the mouth. The adhesive component need not be adhesive when in dry or granular form, such as when present in a lozenge that is not in use, but the adhesive component should at least have adhesive properties when wetted by saliva in the user's mouth.

For example, acacia gum adheres very well to teeth and gingiva and may act as an adhesive in the adherent layer. Alternatively, the lozenge may comprise one or more other adhesive components, such as gelatin, gum Arabic, alginate, starch, pectin, polyvinylpyrrolidone, carboxymethylcellulose (CMC), hydroxymethylcellulose, polyvinyl acid, polyacrylic acid, and Carbopol.

In one approach, the first, adherent layer includes at least about 60 percent adhesive component by weight of the first, adherent layer, in another aspect at least about 70 percent adhesive component, in another aspect at least about 75 percent adhesive component, and in yet another aspect at least about 80 percent adhesive component, in order to provide sufficient adhesiveness to the lozenge for adhering to the inside of a user's mouth. In a preferred aspect, the adhesive component is acacia gum.

It is generally preferred that the adhesive component should be effective to adhere a lozenge (having a mass "X" milligrams) to the roof of a human user's mouth strongly enough to hold the mass of the lozenge plus an additional mass of "2X" milligrams against the force of gravity.

Alkalizer

The lozenge may further comprise an alkalizer (i.e., base) to adjust the pH of the lozenge or layers thereof when mixed with saliva in the mouth. It is well known that acidic pH can be damaging to teeth. Therefore, it may be desired that the lozenge has a neutral or basic pH upon dissolving or otherwise disintegrating in saliva (such as when dissolved in 10 parts water). In one approach, the alkalizer may be calcium carbonate, but any alkalizer that that does not adversely impact the lozenge, such as microbial stability, chemical stability, textural stability, or appearance of the lozenge may be used. Other examples include magnesium carbonate, sodium bicarbonate, potassium bicarbonate, sodium carbonate, magnesium hydroxide, aluminum hydroxide, $C_7H_5HiO_4$, and combinations thereof.

It is noted that the adhesiveness of acacia gum, in particular, can be somewhat reduced when too much alkalizer, such as calcium carbonate, is included in the same layer of the lozenge. Therefore, effective ratios of calcium carbonate to acacia gum range from about 1:15 to about 1:50.

The alkalizer may be present in the adherent layer, in the second layer, or in both the adherent and second layers. In one aspect, the alkalizer is included in an amount of about 1 to about 10 percent by weight of the layer, in another aspect about 2 to about 8 percent by weight of the layer, and in another aspect about 3 to about 6 percent by weight of the layer.

Other Components

The first, adherent layer and second layer of the lozenge may further include a variety of other ingredients or excipients, such as one or more binders, fillers (e.g., bulking agents), medicaments, vitamins, salts, buffers, lubricants (e.g., calcium stearate and/or magnesium stearate), and combinations thereof. These ingredients can be selected to provide desired flow, hardness, taste, and/or compression characteristics to the ingredients of each layer of the lozenge.

In one aspect, the ingredients of the oral adhering lozenge may be selected to provide a desired dissolution time when adhered in a user's mouth, such as ranging from about 1 minute to about 8 hours.

Suitable binder materials to strengthen the non-adherent layer of the lozenge include, for example, acacia gum, polyvinyl pyrrolidone, maltodextrin, sorbitol, lactose, and cellulose gum. To ensure the lozenge erodes at a desired rate in the mouth, the lozenge may include a binder that dissolves slowly in saliva or mucosa. Optionally, the binder may be made with slowly dissolving hydrocolloids so that the lozenge lasts in the mouth for at least about ten minutes and up to about six hours. Suitable binders that dissolve slowly in saliva include collagen, gelatin, carrageenan (particularly in kappa form), xanthan gum, konjac gum, guar gum, locust bean gum, agar, cellulose gum (such as carboxymethylcellulose, hydroxypropylcellulose, and hydroxypropylmethylcellulose), starch (such as corn starch or pregelatinized starch, such as pregelatinized corn starch), and combinations thereof.

Embodiment including CBD

In one particular approach, primary and secondary flavor-masking components may be used to mask CBD in an adhering lozenge. In the lozenge, the dose of CBD may be at least about 5 mg of CBD, in another aspect at least about 10 mg of CBD, and in another aspect at least about 15 mg of CBD. In one approach, the lozenge may include about 2 to about 5 percent CBD by weight of the adherent layer, by weight of the second, non-adherent layer, or by weight of each of the adhering and second layers. To mask the undesirable flavor of CBD, the lozenge may include about 0.5 to about 5 weight percent primary flavor-masking component (such as flavor oil) in the first, adherent layer and about 0.5 to about 3.5 weight percent primary flavor-masking component (such as a flavor oil) in the second, non-adherent layer. In addition to the primary flavor-masking component, the lozenge may further include about 10 to about 20 weight percent secondary flavor-masking component in either layer, in another aspect about 45 to about 55 weight percent secondary flavor-masking component in either layer.

For example, in one embodiment, when a flavor oil such as mint oil is used as a primary flavor-masking component used to mask the undesirable flavor of CBD, the ratio of primary flavor-masking component to CBD is about 0.5:1 to about 0.7:1 in the first, adherent layer and about 0.4:1 to about 0.6:1 in the second layer, with the adherent layer having more masking flavor relative to the amount of CBD than in the non-adherent layer. In one aspect, the bitter CBD active component can be omitted entirely from the first, adherent layer, thereby giving an infinite ratio of masking flavor to CBD.

Method of Making the Lozenge

In one approach, it has been found to be advantageous that the ingredients of each layer of the lozenge be combined when in granular form. Two or more of the powders may be "granulated" together such that they adhere to each other in larger grains or granules. In granulation, dispersed small particles or powders are formed into larger grains by creating bonds between particles. Bonds may be formed by compression or by using a binding agent. The granulation process may be a wet granulation process or a dry granulation process. Granulation methods can be employed for the first, adherent layer, the second layer, or both layers.

For example, when a small amount of active component (or a flavor-masking component) is included in a formulation, it can be challenging to equally distribute that component throughout the product. This may be the result of the component being of different size particle, density, compressibility, or moisture content than other ingredients of the layer. This can cause the active (or other ingredient) to segregate or otherwise separate from the other ingredients during blending or other method steps such that it is not equally distributed in the final product. Such uneven distribution can adversely impact the ability to deliver a consistent dosage of active or flavoring, for example. To address this, the active component and/or flavor-masking component can be granulated alone or with other ingredients of the lozenge layer. When an active component and/or flavor-masking component is combined with other ingredients, granulation will provide granules containing a relatively equal distribution of each of the ingredients.

By whichever method is used to prepare the respective layers of the lozenge, it is preferred that the flavor-masking component is homogeneously distributed in the layer(s) and the active component is homogeneously distributed in the layer(s). In one aspect, the flavor-masking component is homogeneously dispersed in the first, adherent layer. In another aspect, the flavor-masking component is homogeneously dispersed in the second layer. In another aspect, the active component is homogeneously dispersed in the second layer. In another aspect, the active component is homogeneously dispersed in the first, adherent layer. In another aspect, the flavor-masking component and active component are both homogeneously dispersed in the first, adherent layer. In another aspect, the flavor-masking component and active component and active component are both homogeneously dispersed in the second layer.

In a wet granulation process, a liquid solution (such as an aqueous liquid or other solvent, such as a polyvinyl pyrrolidone) may be applied to a powdered ingredient or a powdered mixture of ingredients. The aqueous liquid or other solvent is then evaporated from the mixture to provide a denser mass. The mass may then be milled to provide granules of desired size. In another approach, a granulator may be used to combine powders and liquid binder. A fluid-bed granulator or air flow tumbler uses air flow to suspend powders in a chamber while a liquid may be sprayed onto the powder. In yet another approach, a binder solution and powders may be mixed, milled, and then spread on trays or sheets before being dried in a dryer for a suitable amount of time to provide a desired moisture content. One or more excipients, as discussed above, may be included to provide desired characteristics during the granulation process.

In one particular approach, the active component with an undesirable flavor may be granulated with a flavor-masking component. For example, the component with an undesirable flavor may be coated, such as by spraying or vibrating, onto grains of the flavor-masking component or grains comprising the flavor-masking component. In one aspect, the active component could be sprayed onto polyol grains, lactose grains, and/or acacia gum grains. In another aspect, the active component can be sprayed onto polyol grains, lactose grains, and/or acacia gum grains that have already been mixed with a flavor-masking component. For example, by coating an active component that has an undesirable flavor onto grains that release a masking flavor, the flavor-masking component and active component with undesirable flavor will both be released at about the same time, thus reducing or eliminating the perceptibility of the undesirable flavor.

In another approach, the active component may be granulated with a binder or other excipient to form active-containing granules. In one aspect, the active component could be granulated with polyol grains and/or acacia gum. Further, the flavor-masking component may be separately granulated with a binder or other excipient to form flavor-masking granules. The active-containing granules may then be combined with flavor-masking granules to provide the desired relative amounts within a layer of the lozenge.

The oral adhering lozenge may then be manufactured using a tablet press. The powders and/or granules may be pressed into the respective layers of the lozenge using a bi-layer tablet press. A suitable method of forming a bi-layer lozenge with a bi-layer tablet press is described in U.S. Pat. No. 8,865,133, granted on Oct. 21, 2014, which is incorporated herein by reference. In one aspect, the lozenge may be formed by pressing powders of polyol crystals, one or more gums, and any other ingredients into a tablet with a tablet press. Xylitol grains of about 50 to about 350 microns are preferred. The grains may be granulated with a coating of gum on the outside, such as Danisco Xylitab 200, which is granulated with up to but less than 2% carboxymethylcellulose (CMC) as a compression binder.

For instance, when making bilayer lozenges with a typical press, a first powder/granules or a combination of powders and/or granules is placed in the die, sitting on the lower punch, then the upper punch tamps the powders, leaving the surface having the shape of the upper punch face. Powders and/or granules of the second layer are then added and the punch is pressed again to form the bilayer lozenge.

A lozenge may be pressed into two layers which when combined may take the shape generally shown in the FIGURE. The adhering lozenge may be formed in a variety of shapes, sizes, and configurations. For example, when viewed from the top, the lozenge may be a variety of shapes, but oval or round shapes are generally preferred. The shape may depend on a number of factors, such as ease and cost of manufacturing, consumer preference, intended surface for adherence within the user's mouth, and/or the desired length of lozenge dissolution in the mouth.

In one aspect, the lozenge may have minimum dimensions of about 5 millimeters by about 5 millimeters. In another aspect, a lozenge will range from about 5 to about 20 mm, in another aspect from about 5 to about 18 mm, in another aspect from about 7 to about 18 mm, and in yet another aspect from about 10 to about 15 mm in at least two dimensions. When the lozenge is round or nearly round, the size range represents suitable diameters. The thickness of a lozenge will generally be from about 1 mm to about 10 mm, and in another aspect from about 4 mm to about 7 mm. In one approach, such a lozenge may be about 100 mg to about 800 mg in weight.

In another aspect, the relative thicknesses of the first, adherent layer and second layer may be the same or different. In one approach, the first, adherent layer may be thinner (and/or have a smaller mass) than the second layer, such as shown in the FIGURE. In this approach, the thickness of the second layer may provide a slowly dissolving active ingredient release layer. Alternatively, the second layer may be thinner than the first, adherent layer. In this approach, an active ingredient included in the second layer may be delivered more quickly while a flavor-masking ingredient may be delivered from a thicker adherent layer for a longer period of time. In yet another approach, the first, adherent layer may be approximately the same thickness (and/or have the same approximate mass) as the second, non-adherent layer.

Advantages and embodiments of the bilayer lozenge compositions described herein are further illustrated by the following examples; however, the particular conditions, processing schemes, materials, and amounts thereof recited in these examples, as well as other conditions and details, should not be construed to unduly limit the compositions and methods described herein. All percentages in this application are by weight unless otherwise indicated.

EXAMPLES

The following examples are presented by way of illustration and not by way of limitation on the scope of the invention.

Example 1

An oral adhering lozenge can be manufactured with CBD (cannabidiol) as the active ingredient having the formulation according to Table 1 below. CBD can be released in the mouth from the lozenge for absorption through the oral mucosa. CBD generally has a bitter flavor but can be masked by a flavor component such as mint oil. It has been found that xylitol by itself is insufficient to mask the bitter flavor from CBD. The ratio of mint to CBD is higher in the first, adherent layer than in the second, non-adherent layer.

TABLE 1

| Ingredients | Weight Percent (wt. %) |
|---|---|
| FIRST, ADHERENT LAYER (165 milligrams total) | |
| Acacia Gum | 74.9 |
| Calcium Carbonate | 2 |
| CBD | 3.8 |
| Xylitol, fine grain | 17 |
| Mint oil | 2.3 |
| TOTAL | 100.0 |
| Ratio Mint/CBD | 0.61 |
| SECOND, NON-ADHERENT LAYER (185 milligrams total) | |
| Acacia Gum | 47.3% |
| Calcium Carbonate | 2.9% |
| CBD | 5.6% |
| Xylitol, fine grain | 17% |
| Mint oil | 2.8% |
| Lactose | 24.4% |
| TOTAL | 100.0% |
| Ratio Mint/CBD | 0.50 |

The adhering lozenge can be made by mixing powders for the first, adherent layer; mixing powders for the second, non-adherent layer; and pouring each mixture into a separate hopper in a bi-layer tablet press.

In this embodiment, the adherent layer has a mint oil:CBD ratio of about 0.61:1, and the second layer has a mint oil:CBD ratio of about 0.50:1. Accordingly, the ratio of flavor-masking component to active agent is higher in the first, adherent layer than in the second layer, thereby providing increased release of the flavor-masking component as the lozenge degrades in the mouth and also providing increased masking of any bitter aftertaste of the CBD.

Example 2

An oral adhering lozenge can be manufactured with CBD (cannabidiol) as the active ingredient having the formulation according to Table 2 below. In this embodiment, the ratio of mint to the CBD is greater in the adherent layer than in the second layer because there is no CBD in the adherent layer.

TABLE 2

| Ingredients | Weight Percent (wt. %) |
|---|---|
| FIRST ADHERENT LAYER (165 milligrams total) | |
| Acacia Gum | 78.5 |
| Calcium Carbonate | 2.5 |
| CBD | 0 |
| Xylitol, fine grain | 16.7 |
| Mint oil | 2.3 |
| TOTAL | 100.0 |
| SECOND LAYER (260 milligrams total) | |
| Acacia Gum | 41.3 |
| Calcium Carbonate | 2.0 |
| CBD | 3.9 |
| Xylitol, fine grain | 50.8 |
| Mint oil | 2.0 |
| TOTAL | 100.0 |
| Ratio Mint/CBD | 0.51 |

The adhering lozenge can be made by mixing powders for the first, adherent layer; mixing powders for the second, non-adherent layer; and pouring each mixture into a separate hopper in a bi-layer tablet press. Those skilled in the art will recognize that a wide variety of other modifications, alterations, and combinations can also be made with respect to the above described embodiments without departing from the scope of the invention, and that such modifications, alterations, and combinations are to be viewed as being within the ambit of the inventive concept.

What is claimed is:

1. An orally adhering lozenge with a flavor masking component effective to mask an undesirable flavor from an active component, the lozenge comprising:
   a first, adherent layer having a first and second side and comprising an orally adhesive component and a flavor-masking component that is released as the first layer dissolves and/or erodes in a human mouth;
   adhered to a second side of the first layer, a second layer comprising an active component with an undesirable flavor and a flavor-masking component that are released as the second layer dissolves and/or erodes in the human mouth;
   the orally adhesive component in the first layer is configured and included in an amount of at least about 60 percent by weight of the first layer to adhere the orally adhering lozenge to the inside of the human mouth, and, when adhered in the human mouth, the second layer finishes dissolving and/or eroding before the first adherent layer finishes dissolving and/or eroding;
   wherein, if the active is only present in the second layer, the perceivable amount of the flavor-masking component is higher in the first, adherent layer than in the second layer, and
   wherein, if the first adherent layer also comprises the active component, a ratio of the perceivable amount of flavor-masking component to active component in the first adherent layer is higher than a ratio of the perceivable amount of flavor-masking component to active component in the second layer.

2. The lozenge of claim 1, wherein the first, adherent layer further comprises an active component with an undesirable flavor.

3. The lozenge of claim 1, where the adherent layer includes no active component.

4. The lozenge of claim 1, wherein the flavor-masking component comprises one or more of a flavor oil, sweetener, flavor compound, polyol, flavor essence, fruit extract, or combination thereof.

5. The lozenge of claim 1, wherein the flavor-masking component is homogeneously dispersed in the adherent layer.

6. The lozenge of claim 2, wherein the flavor-masking component is homogeneously dispersed in the second layer.

7. The lozenge of claim 1, wherein the active component is homogeneously dispersed in the second layer.

8. The lozenge of claim 2, wherein the active component is homogeneously dispersed in the adherent layer.

9. The lozenge of claim 2, wherein the active component comprises one or more of an antibiotic, aspirin, anti-inflammatory, antacid, vitamin, cannabidiol, antifungal, nicotine, caffeine, chamomile, and combinations thereof.

10. A method for preparing a bilayer orally adhering lozenge effective to mask an undesirable flavor from an active component, the method comprising:
   mixing powders and/or granules comprising an orally adhesive component and a flavor-masking component to form a mixture for a first, adherent layer, wherein the orally adhesive component is included in an amount of at least 60 percent by weight of the first layer to adhere the bilayer orally adhering lozenge to the inside of the human mouth;

mixing powders and/or granules comprising an active component having an undesirable flavor and a flavor-masking component to form a mixture for a second layer;

wherein, if the active is only present in the second layer, the perceivable amount of the flavor-masking component is higher in the first, adherent layer than in the second layer, and wherein, if an active component is included in the mixture for the first, adherent layer, a ratio of the perceivable amount of flavor-masking component to active component in the first, adherent layer is higher than a ratio of the perceivable amount of flavor-masking component to active component in the second layer; and pressing the mixtures for the first, adherent layer and second layer in a bi-layer tablet press to form a bilayer orally adhering lozenge.

11. The method of claim 10, further comprising granulating the active component having an undesirable flavor and the flavor-masking component together to form granules having a homogeneous mixture of the active component and flavor-masking component for forming the second layer.

12. The method of claim 10, further comprising coating the active component having an undesirable flavor onto grains of a binder to form granules.

13. The method of claim 10, further comprising granulating the flavor-masking component with one or more excipients to form granules having a homogeneous mixture of the flavor-masking component for forming the first, adherent layer.

14. The method of claim 10, wherein the amount of active component in the first, adherent layer is zero.

15. The method of claim 10, wherein the active component comprises one or more of an antibiotic, aspirin, anti-inflammatory, antacid, vitamin, cannabidiol, antifungal, nicotine, caffeine, chamomile, and combinations thereof.

16. The method of claim 10, wherein the orally adhesive component comprises acacia gum.

17. The method of claim 10, wherein the flavor-masking component comprises one or more of a flavor oil, sweetener, flavor compound, polyol, flavor essence, fruit extract, or combination thereof.

18. The lozenge of claim 1, wherein the flavor-masking component of the first, adherent layer is the same as the flavor-masking component of the second layer.

19. The method of claim 10, wherein the flavor-masking component of the first, adherent layer is the same as the flavor-masking component incorporated into the second layer.

* * * * *